(12) United States Patent
Nakagaki et al.

(10) Patent No.: US 8,163,148 B2
(45) Date of Patent: Apr. 24, 2012

(54) GAS SENSOR ELEMENT

(75) Inventors: Kunihiko Nakagaki, Nagoya (JP); Hideyuki Suzuki, Kasugai (JP); Osamu Nakasone, Inabe (JP)

(73) Assignee: NGK Insulators, Ltd., Nagoya (JP)

( * ) Notice: Subject to any disclaimer, the term of this patent is extended or adjusted under 35 U.S.C. 154(b) by 775 days.

(21) Appl. No.: 11/967,328

(22) Filed: Dec. 31, 2007

(65) Prior Publication Data

US 2008/0105545 A1    May 8, 2008

Related U.S. Application Data

(63) Continuation of application No. PCT/JP2006/314176, filed on Jul. 18, 2006.

(30) Foreign Application Priority Data

Aug. 2, 2005    (JP) .................................. 2005-223690

(51) Int. Cl.
    *G01N 27/407*    (2006.01)
(52) U.S. Cl. ........................................ 204/426; 501/125
(58) Field of Classification Search .................. 204/424, 204/425, 426; 205/781; 73/23.31; 501/125, 501/153
    See application file for complete search history.

(56) References Cited

U.S. PATENT DOCUMENTS

| | | | |
|---|---|---|---|
| 5,753,893 A * | 5/1998 | Noda et al. ..................... | 219/548 |
| 5,877,406 A * | 3/1999 | Kato ............................. | 73/23.31 |
| 5,902,469 A * | 5/1999 | Kato et al. ..................... | 204/425 |
| 6,284,112 B1 | 9/2001 | Kato et al. | |
| 6,355,152 B1 | 3/2002 | Kato et al. | |
| 2002/0139671 A1 | 10/2002 | Kato et al. | |
| 2004/0188251 A1* | 9/2004 | Kurachi et al. ............... | 204/426 |

FOREIGN PATENT DOCUMENTS

| | | |
|---|---|---|
| EP | 0 845 669 | 6/1998 |
| EP | 1 006 352 | 6/2000 |
| EP | 0 678 740 B1 | 6/2001 |
| JP | 08-271476 A1 | 10/1996 |
| JP | 11-237362 A1 | 8/1999 |
| JP | 2000-028576 A1 | 1/2000 |
| JP | 2002-267633 | 9/2002 |
| JP | 2003-329644 A1 | 11/2003 |
| JP | 2004-292175 A1 | 10/2004 |

* cited by examiner

*Primary Examiner* — Kaj K Olsen
(74) *Attorney, Agent, or Firm* — Burr & Brown

(57) ABSTRACT

A gas sensor element including: a sensor layer in which at least one pair of electrodes are provided in a solid electrolyte for measuring an electromotive force based on a difference in an oxygen concentration between atmospheres; and a heater layer which includes a heater element with a heat generating portion and an electrically insulating layer disposed so as to enclose the heater element and which is configured to heat, by an electric current supplied to the heater element, at least a portion of the solid electrolyte at which the at least one pair of electrodes are provided, the sensor layer and the heater layer being laminated integrally on each other, wherein the electrically insulating layer contains at least one metal oxide selected from the group consisting of alkali metal oxide and alkaline earth metal oxide.

17 Claims, 3 Drawing Sheets

GAS SENSOR ELEMENT

This application is a continuation of the International Application No. PCT/JP2006/314176 filed on Jul. 18, 2006, which claims the benefit under 35 U.S.C. §119(a)-(d) of Japanese Application No. 2005-223690 filed on August 2, the entireties of which are incorporated herein by reference.

BACKGROUND OF THE INVENTION

1. Field of the Invention

The present invention relates to a gas sensor element, and more particularly to a gas sensor element suitably used for a gas sensor to measure oxides such as NO, $NO_2$, $SO_2$, $CO_2$, and $H_2O$ and combustible gases such as CO and CnHm, contained in automobile exhaust emissions and the atmosphere. The invention also relates to a nitrogen oxide (NOx) sensor utilizing such a gas sensor element.

2. Discussion of Related Art

There have been proposed various measuring methods and devices for detecting concentrations of desired gas components such as those described above contained in a measurement gas. For instance, JP-A-8-271476 (Patent Document 1), JP-A-11-237362 (Patent Document 2), and JP-A-2000-28576 (Patent Document 3) disclose a measuring device configured to measure an amount of a desired measurement gas component contained in the measurement gas by measuring an amount of oxygen generated by reduction or decomposition of the measurement gas component. More specifically described, the disclosed measuring device uses a gas sensor element to detect the concentration of the desired gas component contained in the measurement gas. The gas sensor element has a laminar structure formed by laminating a plurality of solid electrolyte layers each having a suitable thickness integrally on each other. Within the laminar-structured element, there are provided a first internal space into which the measurement gas is introduced through a first diffusion controlling passage, a second internal space into which an atmosphere in the first internal space is introduced through a second diffusion controlling passage and in which the measurement gas component existing in the atmosphere is reduced or decomposed, first oxygen pumping means to control an oxygen partial pressure in the first internal space, second oxygen pumping means to pump the oxygen out of the second internal space, and current detecting means to detect a pumping current flowing upon a pumping action of the second oxygen pumping means. The gas sensor element detects the amount of the desired measurement gas component on the basis of the pumping current detected by the current detecting means.

The gas sensor element disclosed in the above-indicated Patent Publications includes at least one pair of electrodes arranged to measure an electromotive force based on a difference in an oxygen concentration between atmospheres, for the purpose of detecting the oxygen concentration in the atmosphere, controlling the pumping action performed by the oxygen pumping means disposed in the element. The at least one pair of electrodes are provided in the solid electrolyte layers which are laminated integrally on each other, and cooperate with the above-indicated internal spaces, diffusion controlling passages, oxygen pumping means, etc., to constitute a sensor layer.

In the gas sensor element having the sensor layer described above, in general, a suitable heater layer is laminated integrally on the sensor layer to provide an integral element structure. The heater layer is constituted by including: a heater element having a heat generating portion; and an electrically insulating layer disposed so as to enclose the heater element. By supplying an electric current to the heater element, at least a portion of the sensor layer at which the pair of electrodes for measuring the electromotive force are provided is heated to a prescribed temperature, whereby an operation of detecting the amount of the desired measurement gas component can be effectively conducted.

The above-described laminar-structured gas sensor element which has been conventionally proposed suffers from the following problem when used for measuring the measurement gas such as exhaust emissions. That is, when an electric current is supplied to the heater element of the heater layer of the gas sensor element and a prescribed pulse voltage is applied thereto, noise signal is generated, so that an output value of the electromotive force detected by the pair of electrodes provided in the sensor layer is influenced by the noise signal and undesirably suffers from fluctuations. In particular, while there is a tendency of reduction in a frequency of the voltage applied to the heater element in accordance with recent digitalization of a control circuit for the gas sensor element, such reduction in the frequency of the voltage to be applied to the heater element causes the fluctuations in the output value described above to become large. In this instance, where the desired measurement gas component in the measurement gas is detected based on the fluctuated output values by controlling the oxygen pumping means, for instance, the gas sensor element does not ensure a sufficiently high degree of accuracy of detecting the measurement gas component.

Patent Document 1: JP-A-8-271476
Patent Document 2: JP-A-11-237362
Patent Document 3: JP-A-2000-28576

SUMMARY OF THE INVENTION

The present invention was made in view of the situations described above. It is therefore an object of the invention to provide a gas sensor element having a laminar structure in which a sensor layer and a heater layer are laminated integrally on each other, which gas sensor element is capable of restraining or preventing an influence of signal noise generated by application of a voltage to the heater element of the heater layer and thereby permitting output values to be obtained with high accuracy and high stability.

To solve the problem indicated above, the present invention provides a gas sensor element comprising: a sensor layer in which at least one pair of electrodes are provided in a solid electrolyte for measuring an electromotive force based on a difference in an oxygen concentration between atmospheres; and a heater layer which includes a heater element with a heat generating portion and an electrically insulating layer disposed so as to enclose the heater element and which is configured to heat, by an electric current supplied to the heater element, at least a portion of the solid electrolyte at which the at least one pair of electrodes are provided, the sensor layer and the heater layer being laminated integrally on each other, the gas sensor element being characterized in that the electrically insulating layer contains at least one metal oxide selected from the group consisting of alkali metal oxide and alkaline earth metal oxide.

In one preferred form of the gas sensor element according to the invention, a total content of the at least one metal oxide in the electrically insulating layer is in a range of 0.1-10 wt %, advantageously in a range of 2.5-5 wt %.

In the gas sensor element according to the invention, the electrically insulating layer is advantageously formed of alumina, or alumina and silica.

In another preferred form of the invention, the alkali metal oxide includes an oxide of Li, Na, or K while the alkaline earth metal oxide includes an oxide of Mg, Ca, Sr, or Ba In still another preferred form of the invention, the electrically insulating layer of the heater layer is enclosed by the solid electrolyte.

In a further preferred form of the invention, the at least one pair of electrodes include a first measuring electrode exposed to an external measurement gas and a reference electrode exposed to a reference gas having a reference oxygen concentration.

The present invention also provides a nitrogen oxide sensor, namely, a co-called NOx sensor, including a gas sensor element constructed as described above, for measuring an amount of a nitrogen oxide component contained in an external measurement gas.

In one preferred form of the nitrogen oxide sensor according to the present invention, the nitrogen oxide sensor comprises, in the sensor layer, a first space into which the external measurement gas is introduced from a gas inlet through a first diffusion controlling passage, a second space into which an atmosphere in the first space is introduced through a second diffusion controlling passage, and a reference-gas space in which a reference gas having a reference oxygen concentration is present.

In another preferred form of the nitrogen oxide sensor according to the invention, the nitrogen oxide sensor further comprises first oxygen-partial-pressure detecting means which includes, as the at least one pair of electrodes, a first measuring electrode disposed so as to be in contact with the external measurement gas and a reference electrode disposed so as to be in contact with the reference gas in the reference-gas space, the first oxygen-partial-pressure detecting means being configured to detect an electromotive force corresponding to a difference in an oxygen concentration between the measurement gas and the reference gas.

In still another preferred form of the nitrogen oxide sensor according to the invention, the nitrogen oxide sensor further comprises main pumping means which includes a first inner pumping electrode and a first outer pumping electrode respectively formed inside and outside of the first space, the main pumping means performing a pumping action with respect to oxygen contained in the measurement gas which has been introduced into the first space from the gas inlet, based on a control voltage applied between the first inner and outer pumping electrodes.

In a yet another preferred form of the nitrogen oxide sensor according to the invention, the nitrogen oxide sensor further comprises measuring pumping means which includes: a second inner pumping electrode which is formed inside of the second space and which reduces or decomposes the nitrogen oxide component contained in the atmosphere that has been introduced from the first space, as a result of contact with the atmosphere; and a second outer pumping electrode formed outside of the second space, the measuring pumping means performing a pumping action with respect to oxygen generated by reduction or decomposition of the nitrogen oxide component contained in the atmosphere which has been introduced from the first space, based on a voltage applied between the second inner and outer pumping electrodes.

In a further preferred form of the nitrogen oxide sensor according to the invention, the nitrogen oxide sensor further comprises auxiliary pumping means which includes a pair of auxiliary pumping electrodes respectively formed inside and outside of the second space, the auxiliary pumping means performing a pumping action with respect to oxygen contained in the atmosphere which has been introduced from the first space, based on an auxiliary pumping voltage applied between the pair of auxiliary pumping electrodes.

In a still further preferred form of the nitrogen oxide sensor according to the invention, the nitrogen oxide sensor further comprises second oxygen-partial-pressure detecting means which includes: a second measuring electrode disposed so as to be in contact with the atmosphere in the first space; and a reference electrode disposed so as to be in contact with the reference gas in the reference-gas space, the second oxygen-partial-pressure detecting means being configured to detect an electromotive force corresponding to a difference in an oxygen concentration between the atmosphere in the first space and the reference gas.

In a yet further preferred form of the nitrogen oxide sensor according to the invention, the nitrogen oxide sensor further comprises third oxygen-partial-pressure detecting means which includes: a third measuring electrode disposed so as to be in contact with an atmosphere in the second space and a reference electrode disposed so as to be in contact with the reference gas in the reference-gas space, the third oxygen-partial-pressure detecting means being configured to detect an electromotive force corresponding to a difference in an oxygen concentration between the atmosphere in the second space and the reference gas.

In another preferred form of the nitrogen oxide sensor according to the invention, the nitrogen oxide sensor further comprises fourth oxygen-partial-pressure detecting means which includes: a fourth measuring electrode which is disposed in the second space and which reduces or decomposes the nitrogen oxide component contained in the atmosphere which has been introduced from the first space; and a reference electrode which is disposed so as to be in contact with the reference gas in the reference-gas space, the fourth oxygen-partial-pressure detecting means being configured to detect an electromotive force corresponding to a difference between an amount of oxygen generated by reduction or decomposition of the nitrogen oxide component contained in the atmosphere which has been introduced from the first space and an amount of oxygen contained in the reference gas.

In the thus constructed gas sensor element of the invention, at least one metal oxide selected from alkali metal oxide and alkaline earth metal oxide is contained in the electrically insulating layer disposed so as to enclose the heater element of the heater layer which is laminated integrally on the sensor layer. The arrangement effectively increases resistance between the heater element and the sensor layer, accordingly the at least one pair of electrodes. Accordingly, even when a voltage is applied to the heater element of the heater layer for heat generation, the influence of the generated signal noise can be effectively restrained or prevented, thereby permitting accurate output values to be obtained from the sensor layer. Thus, the measurement gas component can be detected by the gas sensor element with high accuracy and high stability.

BRIEF DESCRIPTION OF THE DRAWINGS

The above and other objects, features, advantages and technical and industrial significance of the present invention will be better understood by reading the following detailed description of a preferred embodiment of the invention, when considered in connection with the accompanying drawings, in which.

DETAILED DESCRIPTION OF THE INVENTION

To further clarify the present invention, there will be hereinafter described in detail an embodiment of the invention with reference to the drawings.

Figure 1:
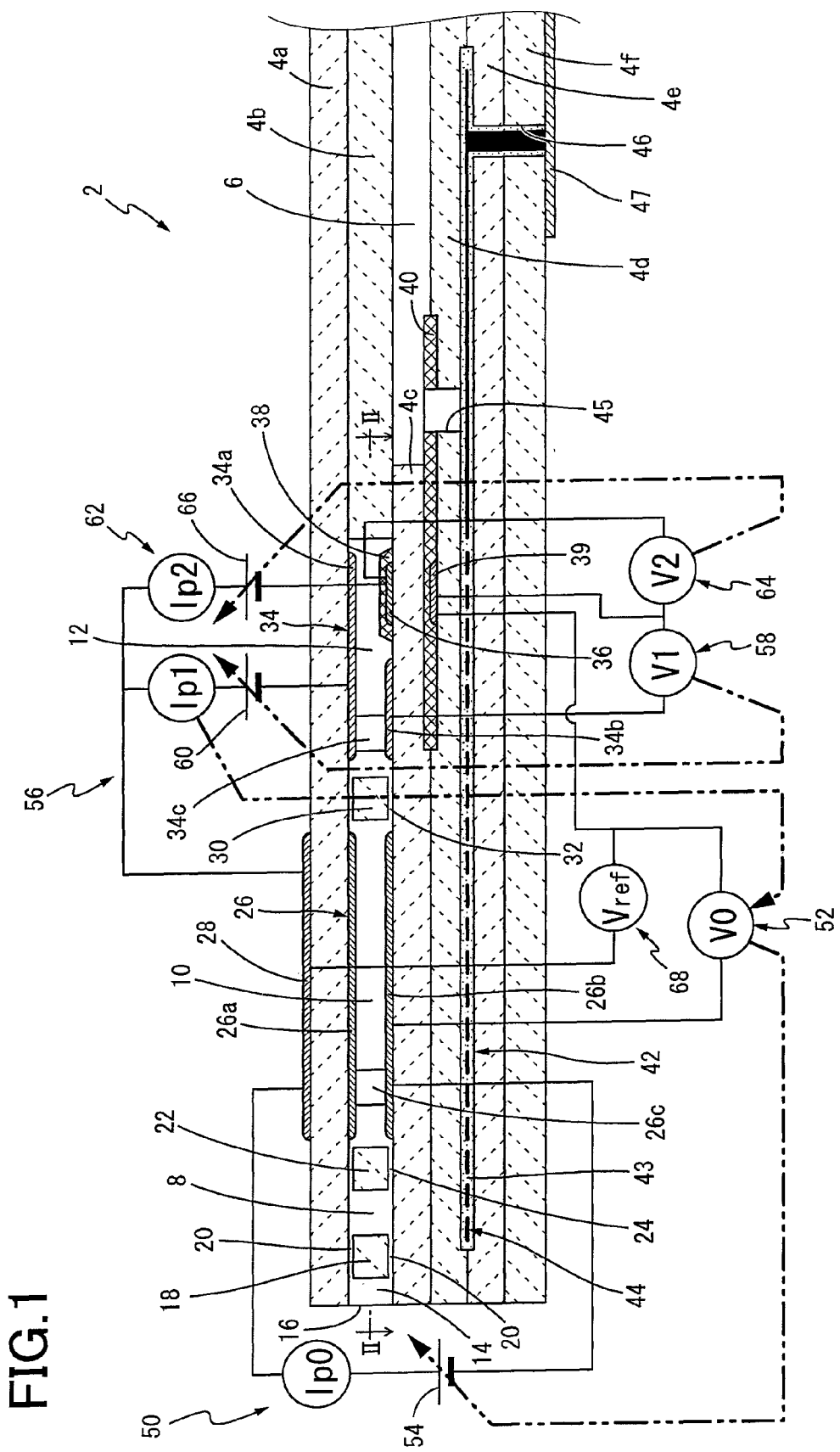
FIG. 1 is an elevational view in longitudinal cross section showing one embodiment of a NOx sensor element as one example of a gas sensor element according to the present invention and also schematically showing a NOx sensor
Figure 2:
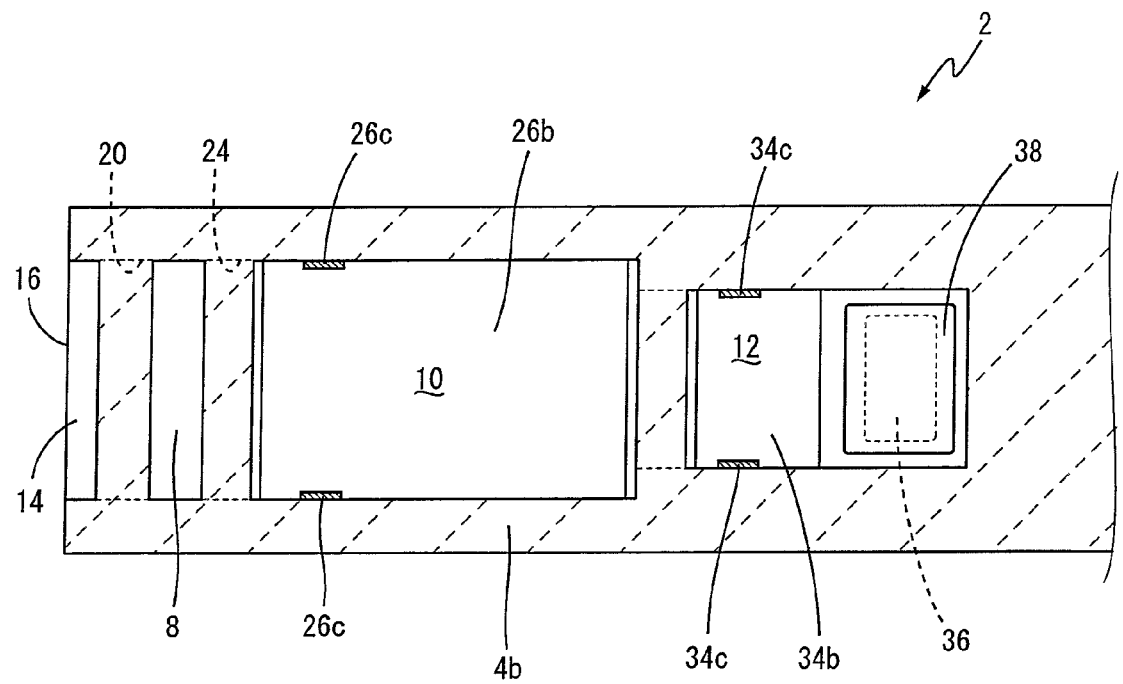
FIG. 2 is a partial cross-sectional view taken along line II-II in FIG. 1.
Figure 3:
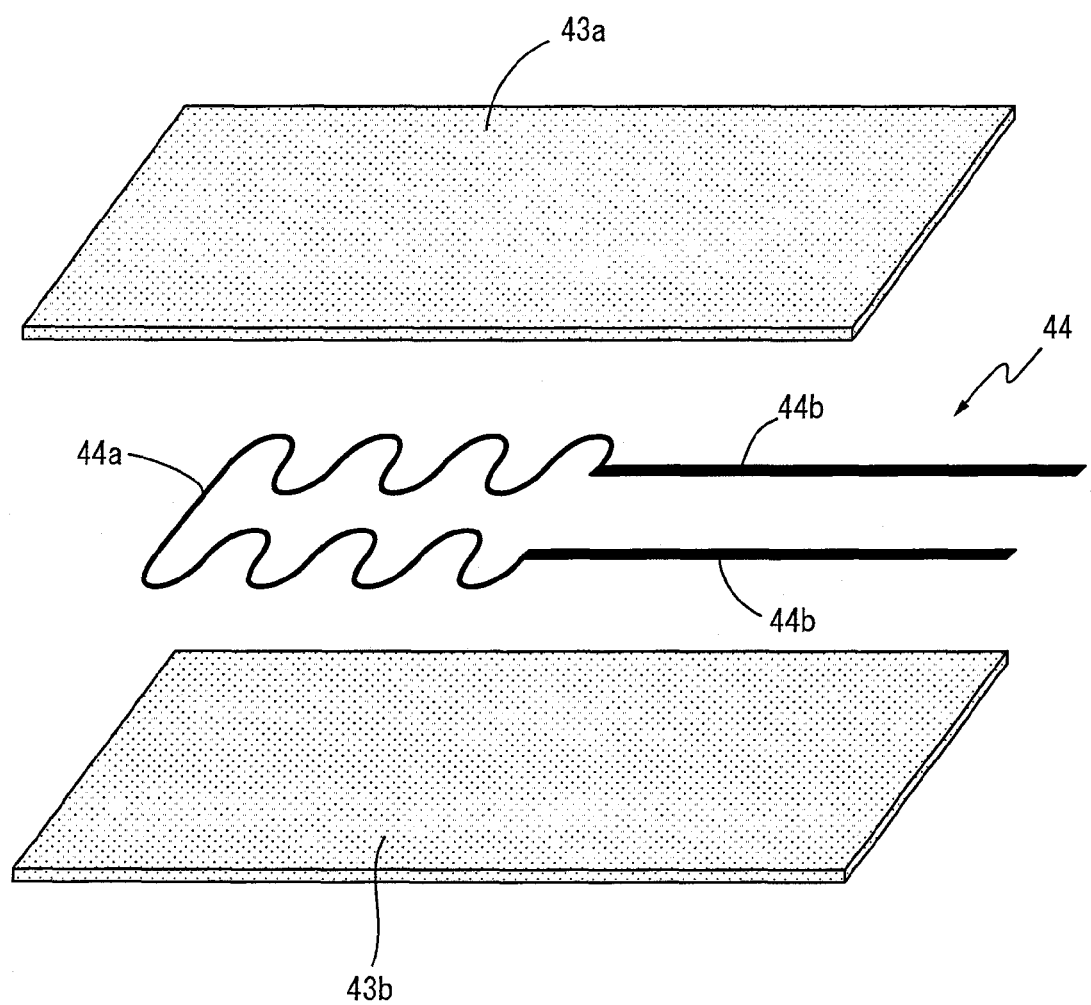
FIG. 3 is an exploded perspective view showing a structure of a heater layer in the NOx sensor element of FIG. 1.

FIGS. 1-3 schematically show a construction of a representative example of a NOx (nitrogen oxide) sensor element as one example of a gas sensor element according to the present invention. FIG. 1 is a view showing a laminar structure of the element in longitudinal cross section. FIG. 2 is a cross-sectional view of the element taken along line II-II in FIG. 1. FIG. 3 is a perspective view showing a heater element and an electrically insulating layer which constitute a heater layer in the NOx sensor element shown in FIG. 1.

The sensor element indicated at 2 in these figures has a generally elongate plate-like shape with a relatively small width and a relatively large length. As shown in FIG. 1, the sensor element 2 has a laminar structure which includes dense and air-tight oxygen-ion conductive solid electrolyte layers 4a, 4b, 4c, 4d, 4e, and 4f which are laminated on each other so as to provide an integral structure. The solid electrolyte layers 4a-4f are formed of a known oxygen-ion conductive solid electrolyte material such as zirconia ceramics. The integral sensor element 2 is easily produced by firing a laminar structure of unfired solid electrolyte layers, as know in the art.

In the integral sensor element 2, an uppermost solid electrolyte layer 4a and a third solid electrolyte layer 4c from the top in FIG. 1 are laminated on each other with a spacer layer in the form of the solid electrolyte layer 4b being interposed therebetween, thereby defining internal spaces which are located between the solid electrolyte layers 4a, 4c and which have a height corresponding to the thickness of the solid electrolyte layer 4b. In other words, as shown in FIG. 1, the internal spaces in which the solid electrolyte layer 4b does not exist are formed so as to extend in a longitudinal direction of the sensor element 2. The sensor element 2 further has a reference-air introducing passage 6 as a reference-gas space which is formed between the solid electrolyte layers 4b, 4d independently of the internal spaces described above. The reference-air introducing passage 6 in which the solid electrolyte layer 4c does not exist is formed so as to extend in the longitudinal direction of the sensor element 2. As known in the art, the reference-air introducing passage 6 is open to the atmosphere at a proximal end of the sensor element 2 (i.e., a right-side in FIG. 1).

As shown in FIGS. 1 and 2, the internal spaces formed between the two solid electrolyte layers 4a, 4c in the sensor element 2 include a buffer space 8, a first space 10, and a second space 12 which are formed independently of each other and arranged in the order of description in the longitudinal direction of the sensor element 2. The buffer space 8 and the first and second spaces 10, 12 have rectangular shapes and predetermined width dimensions in plan view. Further, a clogging-preventive space 14 is formed at a distal end of the sensor element 2 so as to be located between the two solid electrolyte layers 4a, 4c with a height corresponding to the thickness of the solid electrolyte layer 4b, like the buffer space 8 and the first and second spaces 10, 12. The clogging-preventive space 14 in which the solid electrolyte layer 4b as the spacer layer does not exist is open outward, and the open end of the clogging-preventive space 14 is made as a gas inlet 16 through which a measurement gas existing in an external space outside the sensor element 2 is introduced.

The clogging-preventive space 14 and the buffer space 8 are separated from each other by a first partition wall 18 provided by a portion of the solid electrolyte layer 4b. The first partition wall 18 cooperates with the solid electrolyte layers 4a, 4c which are respectively located on upper and lower sides of the first partition wall 18, to define slits at upper and lower portions of the partition wall 18, respectively. The slits have a width substantially equal to that of the buffer space 8 and extend in a width direction of the element. The slits function as first diffusion controlling passages 20 each as first diffusion controlling means. The measurement gas existing in the external space outside the sensor element 2 which has been introduced into the clogging-preventive space 14 through the gas inlet 16 is introduced into the buffer space 8, under a prescribed diffusion resistance, through the first diffusion controlling passages 20 formed on the upper and lower sides of the first partition wall 18.

The buffer space 8 and the first space 10 are separated from each other by a second partition wall 22 provided by a portion of the solid electrolyte layer 4b. Like the first partition wall 18, the second partition wall 22 cooperates with the solid electrolyte layers 4a, 4c which are respectively located near to and remote from the external space, to define slits at upper and lower portions of the second partition wall 22, respectively. The slits that extend in the width direction of the element function as second diffusion controlling passages 24 each as second diffusion controlling means. An atmosphere (measurement gas) existing in the buffer space 8 is introduced into the first space 10, under a prescribed diffusion resistance, through the second diffusion controlling passages 24. The sensor element 2 has main pumping means which is an electrochemical pumping cell constituted by the solid electrolyte layer 4a, an inner pumping electrode 26 and an outer pumping electrode 28 formed on respective inner and outer surfaces of the solid electrolyte layer 4a. By a pumping action of the main pumping means, oxygen in an atmosphere in the first space 10 is pumped out into the external space outside the sensor element 2, or oxygen in the external space is pumped into the first space 10, whereby an oxygen concentration (oxygen partial pressure) in the atmosphere in the first space 10 is controlled to a prescribed value, as known in the art.

The provision of the buffer space 8 and the provision of the slit-like first and second diffusion controlling passages 20, 24 respectively for the first and second partition walls 18, 22 that define the buffer space 8 offer the following advantages. That is, oxygen usually enters abruptly an internal space of the sensor element 2 through the gas inlet 16 due to pulsation of the exhaust gas pressure generated in the measurement gas in the external space. In the arrangement, however, the oxygen in the external space is not directly introduced into the internal space (processing space) of the sensor element 2, but is introduced first into the buffer space 8 through the first diffusion controlling passages 20 and then into the first space as the internal space through the second diffusion controlling passages 24. Accordingly, an abrupt change in the oxygen concentration due to the pulsation of the exhaust gas pressure is absorbed or canceled by the buffer space 8 and the first and second diffusion controlling passages 20, 24 having the buffer space 8 disposed therebetween, so that an influence of the pulsation of the exhaust gas pressure with respect to the internal space (the first space 10) can be substantially ignored, resulting in an improvement in correlation between the oxygen pumping amount by the pumping means in the processing space and the oxygen concentration in the measurement gas.

The arrangement not only improves the measuring accuracy, but also makes it possible to use the internal space as a sensor for detecting an air/fuel ratio. For obtaining the advantages described above, each of the first and second diffusion passages 20, 24 provided for the respective first and second partition walls 18, 22 are made as the slits each in the form of a clearance of 10 μm or smaller.

The clogging-preventive space 14 formed at the distal end portion of the sensor element 2 so as to be open to the external space is provided for preventing clogging of the buffer space 8 at its inlet end with particulate matters (such as soot and oil combustion residue) contained in the measurement gas which is introduced into the buffer space 8 from the external space through the gas inlet 16. Owing to the clogging-preventive space 14, it is possible to measure the NOx component with higher accuracy for a long time period. Thus, the clogging-preventive space 14 is advantageously provided in the sensor element 2.

In the main pumping means disposed in the first space 10, the inner and outer pumping electrodes 26, 28 are generally porous cermet electrodes which are formed of a material consisting of a metal such as Pt and a ceramic material such as $ZrO_2$. In particular, the inner pumping electrode 26 disposed in the first space 10 and exposed to the measurement gas needs to be formed of a material which does not cause a change of the NOx component in the measurement gas, namely, a material having a lowered ability or no ability to reduce or decompose the NOx component such as NO or $NO_2$. For instance, the inner pumping electrode 26 is formed of a compound having a perovskite structure such as $La_3CuO_4$, a cermet material consisting of a metal such as Au having a low catalytic activity and a ceramic material, or a cermet material consisting of a metal such as Au having a low catalytic activity, a metal of the platinum (Pt) group, and a ceramic material.

As shown in FIG. 1, the inner pumping electrode 26 of the main pumping means is formed over the solid electrolyte layers 4a, 4b, 4c which define the first space 10. More specifically described, a ceiling electrode portion 26a of the inner pumping electrode 26 is formed over a portion of the lower surface of the solid electrolyte layer 4a which gives a ceiling surface of the first space 10. A bottom electrode portion 26b of the inner pumping electrode 26 is formed over a portion of the upper surface of the solid electrolyte layer 4c which gives a bottom surface of the first space 10. Further, lateral electrode portions 26c of the inner pumping electrode 26 are respectively formed over portions of the respective lateral surfaces (inner surfaces) of the solid electrolyte layer 4b which give respective lateral wall portions of the first space 10. The lateral electrode portions 26c connect the ceiling electrode portion 26a and the bottom electrode portion 26b. Thus, the inner pumping electrode 26 has a tunnel-like electrode structure in which the inner pumping electrode 26 has a tunnel-like shape at a location where the lateral electrode portions 26c are disposed.

In the illustrated sensor element 2, the first space 10 and the second space 12 are separated from each other by a third partition wall 30 provided by a portion of the solid electrolyte layer 4b. Like the above-described first and second partition walls 18, 22, the third partition wall 30 cooperates with the solid electrolyte layers 4a, 4c to define slits at upper and lower portions of the third partition wall 30, respectively, as shown in FIG. 1. The slits which extend in the width direction of the element and which have a length substantially equal to the width of the second space 12 function as third diffusion controlling passages 32 each as third diffusion controlling means through which the first space 10 and the second space 12 communicate with each other. The atmosphere which exists in the first space 10 and the oxygen concentration (partial pressure) of which has been controlled is introduced into the second space 12 through the third diffusion controlling passages 32 under a prescribed diffusion resistance.

Within the second space 12, there are provided an auxiliary pumping electrode 34 and a measuring electrode 36. The auxiliary pumping electrode 34 cooperates with the solid electrolyte layer 4a and a suitable outer electrode, e.g., the outer pumping electrode 28, to constitute an auxiliary electrochemical pumping cell, thereby controlling the oxygen concentration (partial pressure) in the atmosphere within the second space 12 to a prescribed value. The auxiliary pumping electrode 34 is disposed in the second space 12 so as to have a tunnel-like electrode structure similar to that of the inner pumping electrode 26 disposed in the first space 10. That is, a ceiling electrode portion 34a of the auxiliary pumping electrode 34 is formed over a portion of the lower surface of the solid electrolyte layer 4a that gives a ceiling surface of the second space 12. A bottom electrode portion 34b of the auxiliary pumping electrode 34 is formed over a portion of the upper surface of the solid electrolyte layer 4c that gives a bottom surface of the second space 12. Lateral electrode portions 34c of the auxiliary pumping electrode 34 which connect the ceiling electrode portion 34a and the bottom electrode portion 34b are formed over portions of the respective lateral surfaces of the solid electrolyte layer 4b that give respective lateral walls of the second space 12. Like the inner pumping electrode 26 of the main pumping means described above, the auxiliary pumping electrode 34 is formed of a material having a lowered ability or no ability to cause reduction or decomposition of the NOx component contained in the measurement gas. For instance, the auxiliary pumping electrode 34 is a porous cermet electrode of $Pt—ZrO_2$ containing 1% of Au.

The measuring electrode 36 disposed in the second space 12 needs to be formed of a material that includes a component capable of causing reduction or decomposition of the NOx component which exists in the second space 12 and the oxygen concentration (partial pressure) of which has been controlled. That is, the component in the measuring electrode 36 needs to cause reduction or decomposition of the NOx component as a result of contact with the atmosphere. Here, the measuring electrode 36 is a porous electrode formed of a cermet material consisting of an electrode metal material capable of reducing or decomposing the NOx component in the measurement gas and a ceramic material. As the electrode metal material of the cermet material of which the measuring electrode 36 is formed, a noble metal is advantageously employed. In particular, an alloy of platinum (PT) and rhodium (Rh) is advantageously employed. The ratio of Pt and Rh (Pt:Rh) in the alloy is preferably 100-40 wt %:0-60 wt %. Where the noble metal is used for the electrode metal material, the ratio of the noble metal and the ceramic material (the noble metal/the ceramic material) is advantageously held in a range of 65/35-40/60.

As the ceramic material which is another component of the cermet material of which the measuring electrode 36 is formed, a $ZrO_2$ material is advantageously used for ensuring that the measuring electrode 36 is firmly fixed to the solid electrolyte layer 4c.

As shown in FIG. 1, the measuring electrode 36 disposed in the second space 12 is covered with a porous ceramic layer as an electrode-protective layer 38 formed of a ceramic material such as $Al_2O_3$ and having a predetermined thickness. The electrode-protective layer 38 is for preventing inert components such as a metal vaporized from the auxiliary pumping electrode 34 disposed in the second space 12 from adhering to the measuring electrode 36 and thereby effectively keeping the catalytic activity (NOx decomposing/reducing ability) of the measuring electrode 36.

In the illustrated sensor element 2, a reference electrode 39 is disposed on one of opposite sides of the solid electrolyte layer 4c which is remote from the second space 12, so as to be exposed to the reference air in the reference-air introducing passage 6. The reference electrode 39 is utilized in measuring the oxygen concentrations (partial pressures) in the atmospheres in the first space 10 and the second space 12 as well as the oxygen concentration (partial pressure) in the atmosphere (measurement gas) in the external space. In particular, where oxygen-partial-pressure detecting means as an electrochemical sensor cell is constituted by the measuring electrode 36, the solid electrolyte layers 4c, 4d, and the reference electrode 39, it is possible to detect an electromotive force that corresponds to a difference between the amount of oxygen generated by reduction or decomposition of the NOx component contained in the atmosphere surrounding the measuring electrode 36 and the amount of oxygen contained in the reference air, whereby the concentration of the NOx component in the measurement gas can be obtained. The reference electrode 39 which is formed on the solid electrolyte layer 4d as a seal layer is covered with a porous alumina layer 40 through which the reference air existing in the reference-air introducing passage 6 reaches and contacts the reference electrode 39.

As apparent from the above description, the sensor layer of the sensor element 2 is constituted by the solid electrolyte layers 4a-4d, the internal spaces 6, 8, 10, 12, 14, the electrodes 26, 28, 34, 36, 39, and the porous alumina layer 40.

In the sensor element 2, a plurality of ceramic layers in the form of the solid electrolyte layers 4d-4f are laminated on one side of the solid electrolyte layer 4c which is remote from the internal spaces (8, 10, 12), as shown in FIG. 1. Further, a heater layer 42 is interposed between the two adjacent solid electrolyte layers 4d, 4e so as to be enclosed by the same 4d, 4e. The heater layer 42 is configured to generate heat with an electric power supplied from an external power source. The heater layer 42 is provided to heat the solid electrolyte layers 4a-4f that constitute the sensor element to a prescribed temperature for increasing the oxygen ion conductivity of the solid electrolyte layers 4a-4f. The heater layer 42 includes a heater element 44 and an electrically insulating layer 43 which is formed of alumina or the like for ensuring electrical insulation from the solid electrolyte layers 4d, 4e and which encloses the heater element 44. The heater layer 42 is held in communication with the reference-air introducing passage 6 at the proximal end portion of the sensor element 2, through a pressure-releasing hole 45 that is formed through the solid electrolyte layer 4d, whereby an increase in the internal pressure in the heater layer 42 is mitigated. The heater element 44 of the heater layer 42 is pulled out on the element surface via a through-hole 46 which is formed through the solid electrolyte layers 4e, 4f and an inner periphery of which is electrically insulated from the solid electrolyte layers 4e, 4f. Further, the heater element 44 is brought into conduction with a connector pad 47 formed so as to be insulated from the solid electrolyte layer 4f.

The heater element 44 of the heater layer 42 is configured to heat, to the prescribed temperature, at least portions of the solid electrolyte layers 4a-4c that define the first space 10 and the second space 12. As shown in FIG. 3, the heater element 44 is constituted by a heat generating portion 44a for heating the portions of the solid electrolyte layers 4a-4c in the vicinity of the first and second spaces 10, 12, and current-supplying lead portions 44b, 44b which are connected to respective ends of the heat generating portion 44a and through which a prescribed heater current is supplied to the heat generating portion 44a. The heater element 44 is sandwiched by and between an upper insulating layer 43a and a lower insulating layer 43b that constitute the electrically insulating layer 43, whereby the heater element 44 is enclosed by the electrically insulating layer 43, as shown in FIG. 1. As the electric current supplied to the heat generating portion 44a of the heater element 44 through the current-supplying lead portions 44b, there may be suitably employed a pulse current having a predetermined frequency at which a predetermined voltage is applied. The frequency of the pulse current is generally about 10-1000 Hz, preferably about 50-500 Hz. The prescribed voltage is generally about 8-24 V, preferably about 10-17 V. Due to such a pulse current supplied to the heater element 44, in other words, the pulse voltage applied to the heater element 44, the influence of the signal noise described above becomes striking.

In the NOx sensor element 2 described above, the solid electrolyte layer 4a, and the inner and outer pumping electrodes 26, 28 cooperate with each other to constitute an electrochemical pumping cell, namely, a main pumping cell 50. Further, the solid electrolyte layers 4a-4d, and the inner pumping electrode 26, and the reference electrode 39 cooperate with each other to constitute an electrochemical sensor cell, namely, an oxygen-partial-pressure detecting cell 52 (i.e., second oxygen-partial-pressure detecting means) for controlling the main pumping cell 50, to detect the oxygen concentration (partial pressure) in the first space 10. Reference numeral 54 denotes a variable power source for driving the main pumping cell 50.

The solid electrolyte 4a, the outer pumping electrode 28, and the auxiliary pumping electrode 34 cooperate with each other to constitute an electrochemical pumping cell, namely, an auxiliary pumping cell 56 for controlling the oxygen partial pressure in the atmosphere in the second space 12. Further, the solid electrolyte layers, 4a, 4b, 4c, 4d, the auxiliary pumping electrode 34, and the reference electrode 39 cooperate with each other to constitute an electrochemical sensor cell, namely, an oxygen-partial-pressure detecting cell 58 (i.e., third oxygen-partial-pressure detecting means) for controlling the auxiliary pumping cell 56, to detect the oxygen partial pressure in the second space 12. The auxiliary pumping cell 56 is driven by a variable power source 60 the voltage of which is controlled by the oxygen-partial-pressure detecting cell 58. A pumping current Ip1 of the auxiliary pumping cell 56 is used to control an electromotive force V0 of the oxygen-partial-pressure detecting cell 52.

The solid electrolyte layers 4a, 4b, 4c, the outer pumping electrode 28, and the measuring electrode 36 cooperate with each other to constitute an electrochemical pumping cell, namely, a measuring pumping cell 62 for pumping out oxygen generated by decomposition of the nitrogen oxide (NOx) contained in the atmosphere surrounding the measuring electrode 36, to detect an amount of the oxygen generated. The solid electrolyte layers 4a, 4b, 4c, 4d, the measuring electrode 36, and the reference electrode 39 cooperate with each other to constitute an electrochemical sensor cell, namely, an oxygen-partial-pressure detecting cell 64 (fourth oxygen-partial-pressure detecting means) for controlling the measuring pumping cell 62, to detect the oxygen partial pressure in the atmosphere surrounding the measuring electrode 36. The measuring pumping cell 62 is driven by a variable power source 66 the voltage of which is controlled on the basis of an electromotive force V2 detected by the oxygen-partial-pressure detecting cell 64. A pumping current Ip2 of the measuring pumping cell 62 which corresponds to the concentration of the nitrogen oxide contained in the measurement gas is thus obtained.

The solid electrolyte layers 4a, 4b, 4c, 4d, the outer pumping electrode 28, and the reference electrode 39 cooperate with each other to constitute an electrochemical sensor cell 68 (first oxygen-partial-pressure detecting means). An electromotive force Vref obtained by the sensor cell 68 is used to detect the oxygen partial pressure (concentration) in the measurement gas existing in the external space outside the sensor.

The concentration of the nitrogen oxide (NOx) in the measurement gas is detected in the following manner, using the NOx sensor constructed as described above. Initially, the external measurement gas is introduced into the buffer space 8 from the clogging-preventive space 14 formed in the distal end portion of the sensor element 2, through the slit-like first diffusion controlling passages 20 formed at the upper and lower portions of the first partition wall 18. The atmosphere thus introduced into the buffer space 8 is then introduced into the first space 10 through the slit-like second diffusion controlling passages 24 formed at the upper and lower portions of the second partition wall 22. The voltage of the variable power source 54 is controlled such that the electromotive force V0 of the oxygen-partial-pressure detecting cell 52 is held constant, so that a pumping current Ip0 of the main pumping cell 50 is controlled. In this respect, the oxygen partial pressure in the atmosphere in the first space 10 is controlled to a prescribed value, e.g., about $10^{-7}$ atm.

The atmosphere is then introduced from the first space into the second space 12 through the slit-like third diffusion controlling passages 32 formed at the upper and lower portions of the third partition wall 30. The atmosphere thus introduced into the second space 12 is subjected to a pumping action by the auxiliary pumping cell 56 to pump oxygen in the atmosphere, with an electric power supplied from the variable power source 60 whose voltage is controlled on the basis of an electromotive force V1 detected by the oxygen-partial-pressure detecting cell 58. Thus, the oxygen partial pressure in the atmosphere in the second space 12 is controlled to a low value at which the measurement of the nitrogen oxide is not substantially influenced. The pumping current Ip1 of the auxiliary pumping cell 56 is fed, as a control signal, to the oxygen-partial-pressure detecting cell 52, whereby the electromotive force V0 of the same 52 is controlled. As a result, a gradient of the oxygen partial pressure in the atmosphere is held constant in the second space 12 between the third diffusion controlling passages 32 and the auxiliary pumping electrode 34.

The atmosphere in the second space 12 the oxygen partial pressure of which has been controlled reaches the measuring electrode 36 through the electrode-protective layer 38, under the prescribed diffusion resistance. The nitrogen oxide in the atmosphere which has reached the measuring electrode 36 is reduced or decomposed around the measuring electrode 36 to generate oxygen. The thus generated oxygen is pumped by the measuring pumping cell 62. In this instance, the voltage of the variable power source 66 is controlled such that an electromotive force V2 of the oxygen-partial pressure detecting cell 64 is held constant. Here, the amount of oxygen generated around the measuring electrode 36 is proportional to the concentration of the nitrogen oxide in the measurement gas. Accordingly, the concentration of the nitrogen oxide (NOx) in the desired measurement gas can be calculated based on the pumping current Ip2 of the measuring pumping cell 62.

When the concentration of NOx existing in the external measurement gas is measured using the NOx sensor that employs the sensor element 2 constructed as described above, an electric current is supplied to the heater element 44 through the connector pad 47 to keep the temperature of the element in a range effective or suitable for the measurement, and a prescribed pulse voltage is applied to the heater element 44. In this instance, there is generated signal noise due to the application of the voltage to the heater element 44, causing fluctuations in output values (electromotive force values detected) by the oxygen-partial-pressure detecting cells 52, 58, 64, 68 each for measuring the electromotive force based on a difference in the oxygen concentration between the atmospheres. In particular, the sensor cell 68 as the oxygen-partial-pressure detecting cell for detecting the electromotive force Vref by the outer pumping electrode 28 and the reference electrode 39 suffers from large fluctuations in its output values.

In the light of the above, the electrically insulating layer 43 of the heater element 44 in the illustrated sensor element 2 contains at least one metal oxide selected from the group consisting of alkali metal oxide and alkaline earth metal oxide, whereby a resistance between the heater element 44 and the sensor layer can be advantageously enhanced, so that the influence of the signal noise caused when the electric current is supplied to the heater element 44 can be effectively restrained or prevented.

The oxide of alkali metal or alkaline earth metal which exhibits excellent effect of restraining or preventing the influence of the signal noise includes an oxide of Li, Na, K or the like and an oxide of Mg, Ca, Sr, Ba or the like. Such oxide is used alone or in combination, and is contained in a constituent material of the electrically insulating layer 43 in the form of an oxide or in the form of a compound capable of forming an oxide when fired.

The amount of the metal oxide contained in the electrically insulating layer 43 is suitably determined depending upon the material of the electrically insulating layer 43, the kind of the metal oxide, and the desired degree of the action or the effect to be obtained. The total content of the metal oxide in the electrically insulating layer 43 is generally in a range of 0.1-10 wt %, preferably in a range of 2.5-5 wt. %. Where the amount of the metal oxide contained in the electrically insulating layer 43 is excessively small, it is difficult to obtain a sufficiently high degree of effect of restraining the signal noise. On the other hand, an excessively large amount of the metal oxide in the electrically insulating layer 43 makes it difficult to form the integral laminar-structured element by cofiring the heater layer 42 and the sensor layer (constituted by the solid electrolyte layers 4a-4d, the internal spaces 6, 8, 10, 12, 14 formed therein, the electrodes 26, 28, 34, 36, 39, etc.). The total amount of the metal oxide [or the compound capable of forming the metal oxide as a result of firing] contained in the electrically insulating layer 43 is adjusted as described above, thereby advantageously enhancing the resistance value between the heater element 44 and the sensor layer, more specifically, the electrodes of the respective oxygen-partial-pressure detecting cells 52, 58, 64, 68. In consequence, the electrically insulating layer 43 and accordingly the heater layer 42 can be easily formed while effectively restraining or preventing the influence of the signal noise generated from the heater layer 42, so that the integral laminar-structured gas sensor element 2 can be advantageously produced.

The electrically insulating layer 43 in which the at least one specific metal oxide is contained is formed using an electrically insulating ceramic material such as alumina or spinel known in the art. In the present invention, the electrically insulating layer 43 is preferably formed using alumina or a mixture of alumina and silica. The electrically insulating layer 43 is formed generally in a porous structure. Owing to the electrically insulating layer 43 formed of alumina or the mixture of alumina and silica, it is possible to more effectively attain the effect of restraining or preventing the influence of the signal noise, based on the enhanced resistance as a result of the addition of the at least one specific metal oxide according to the present invention.

While there have been explained in detail one embodiment of the gas sensor element of the invention and one example of the sensor in the form of the nitrogen oxide (NOx) sensor using the sensor element, it is to be understood that the present invention is not limited to the illustrated embodiment and example and that the present invention may be embodied with various changes, modifications, and improvements, which may occur to those skilled in the art, without departing from the spirit of the invention.

As the structure of the sensor element, any known structure may be adopted, provided that the sensor element has a structure in which the sensor layer and the heater layer are laminated integrally on each other and in which the sensor layer has at least one pair of electrodes provided in the solid electrolyte in the form of the plurality of solid electrolyte layers, so as to measure the electromotive force based on a difference in the oxygen concentration between the atmospheres to which the respective electrodes are exposed. While the measuring electrodes (28, 26, 34, 36) in the respective sensor cells (68, 52, 58, 64) function also as the pumping electrodes of the respective pumping cells (50, 56, 62) in the illustrated sensor element 2, the measuring electrodes may be constituted by other electrodes separate from the pumping electrodes. Further, while the reference-gas space and the reference electrode are common to the sensor cells as illustrated above, the reference-gas space and the reference electrode may be provided by other spaces and other electrodes respectively provided for the individual sensor cells.

While the sensor element 2 according to the illustrated embodiment has the clogging-preventive space 14 formed between the gas inlet 16 and the first partition wall 18, the clogging-preventive space 14 may be eliminated. Instead of providing the clogging-preventive space 14, the first partition wall 18 may be formed such that the inlet ends of the respective first diffusion controlling passages 20 are located at the gas inlet 16. Further, the configurations of the second and third diffusion controlling passages 24, 32 may not be limited to those in the illustrated embodiment.

The gas sensor element according to the present invention can be used not only for a sensor to measure the nitrogen oxide (NOx) in the measurement gas, but also for sensors to measure components other than NOx which are influenced by oxygen existing in the measurement gas and which contain bound oxygen, such as sensors to measure $H_2O$ and $CO_2$. For instance, the gas sensor element according to the present invention can be used for a gas sensor configured to pump out $O_2$ generated by electrolysis of $CO_2$ or $H_2O$, and a gas sensor configured to perform a pumping action with respect to $H_2$ generated by electrolysis of $H_2O$, using a proton-ion conductive solid electrolyte. Further, it is noted that an oxygen sensor is the simplest form of the gas sensor element in which the pair of electrodes are exposed to the atmospheres having mutually different oxygen concentrations and which is configured to measure the electromotive force based on a difference in the oxygen concentration between the atmospheres. It is to be understood that the present invention is applicable to such an oxygen sensor.

EXAMPLES

Hereinafter, representative examples of the present invention will be described to further clarify the invention. It is to be understood that the invention is not limited to the details of the examples.

Various sensor elements (2) each having the structure shown in FIG. 1 were produced by a method similar to that known in the art. Described more specifically, unfired tapes or green sheets of the solid electrolyte ($ZrO_2$) which give the solid electrolyte layers (4a-4f) were laminated on each other. Electrode pastes for forming cermet electrodes by firing were printed on suitable portions of the green sheets for the respective solid electrolyte layers (4a, 4b, 4c, etc.). The green sheets for the solid electrolyte layers (4b, 4c) were subjected to a pressing operation to form openings that give the clogging-preventive space (14), the buffer space (8), the first space (10), the second space (12), and the reference-air introducing passage (6). The green sheets for the solid electrolyte layers (4d, 4e, 4f) were subjected to a punching operation to form the pressure-releasing hole (45) and the through-hole (46). The green sheets for the solid electrolyte layers (4d, 4e) were laminated on each other with a layer for the heater layer (42) (including the upper insulating layer 43a, the heater element 44, and the lower insulating layer 43b) being interposed therebetween. Further, in order to form the slit-like first, second, and third diffusion controlling passages (20, 24, 32), layers with a suitable thickness formed of theobromine which disappears upon firing were provided on portions of upper and lower surfaces of the green sheet for the solid electrolyte layer (4b) that correspond to the first, second, and third partition walls (18, 22, 30) and on portions of surfaces of the green sheets for the solid electrolyte layers (4a, 4c) facing the above-indicated portions of the green sheet for the solid electrolyte layer (4b). The thus obtained green laminar structures were fired into the sensor elements (2) each having the intended structure.

In producing each of the sensor elements (2), various layers including alumina, 2.5% of silica, and suitable amounts of various metal oxides or compounds capable of forming metal oxides by firing, as indicated in the following TABLE 1, were printed to form the electrically insulating layers (43) (each consisting of the upper insulating layer 43a and the lower insulating layer 43b) of the heater layers (42) of the sensor elements (2). Thus, there were obtained the sensor elements (2) in which respective suitable amounts of various metal oxides were contained in the respective electrically insulating layers (43).

Subsequently, there was applied a pulse voltage of 14 V with a frequency of 100 Hz to the heater element (44) of the heater layer (42) of each of the thus obtained sensor elements (2), so as to heat the temperature of each element to 850° C., and there was measured, by using an impedance analyzer, an alternating-current resistance value between the outer pumping electrode (28) and the heater element (44) in each of the sensor elements (2). The results of the measurement are indicated also in the TABLE 1. It is noted that a larger alternating-current resistance value indicates a higher degree of effect of preventing the influence of the signal noise generated from the heater element (44) with respect to the sensor layer side.

TABLE 1

| Example No. | Content in Electrically Insulating Layer (43) (wt %) | | | | | | | | Alternating-Current Resistance Value (KΩ) |
|---|---|---|---|---|---|---|---|---|---|
| | $Li_2O$ | $Na_2O$ | $K_2O$ | MgO | CaO | SrO | BaO | Total | |
| 1 | 1.5 | 2 | 1.5 | — | — | — | — | 5.0 | 180.4 |
| 2 | — | 5 | — | — | — | — | — | 5.0 | 208.7 |
| 3 | — | — | — | — | 5 | — | — | 5.0 | 150.3 |
| 4 | — | — | — | 0.6 | 2 | — | 2.4 | 5.0 | 120.1 |
| 5 | — | — | — | — | 3.75 | — | — | 3.75 | 110.6 |
| 6 | — | — | — | 0.45 | 1.5 | — | 1.8 | 3.75 | 105.3 |
| 7 | — | — | — | — | 1.25 | 1.25 | — | 2.5 | 98.5 |
| 8 | — | — | — | 0.3 | 1 | — | 1.2 | 2.5 | 78.4 |
| 9 | — | — | — | 0.15 | 0.5 | — | 0.6 | 1.25 | 42.3 |
| 10 | — | — | — | — | — | — | 0.5 | 0.5 | 21.5 |
| 11 | — | — | 0.05 | 0.05 | — | — | — | 0.1 | 5.2 |
| 12 | — | 2.5 | — | 2.5 | 2.5 | 2.5 | — | 10.0 | 312.3 |
| 13 | — | — | — | — | — | — | — | 0.0 | 0.6 |

As apparent from the results indicated in the TABLE 1, considerably higher alternating-current resistance values were obtained in the sensor elements according to Example Nos. 1-12 whose electrically insulating layers (43) contained at least one metal oxide selected from the alkali metal oxide and the alkaline earth metal oxide, than in the sensor element according to Example No. 13 whose electrically insulating layer (43) contained no metal oxides. Accordingly, it is recognized that the resistance value between the sensor layer and the heater layer in each sensor element was effectively increased owing to the addition of the metal oxide in the electrically insulating layer. Accordingly, it is understood that the adverse influence of the signal noise generated from the heater element (44) can be effectively reduced, so that the fluctuations in the output values in the sensor layer can be advantageously restrained or prevented.

What is claimed is:

1. A gas sensor element comprising: a sensor layer in which at least one pair of electrodes are provided in a solid electrolyte for measuring an electromotive force based on a difference in an oxygen concentration between atmospheres; and a heater layer which includes a heater element with a heat generating portion and an electrically insulating layer disposed so as to enclose the heater element and which is configured to heat, by an electric current supplied to the heater element, at least a portion of the solid electrolyte at which the at least one pair of electrodes are provided, the sensor layer and the heater layer being laminated integrally on each other,
wherein the electrically insulating layer contains at least one metal oxide selected from the group consisting of alkali metal oxide and alkaline earth metal oxide,
wherein at least one electrode of the at least one pair of electrodes has a tunnel-like structure comprising a ceiling electrode portion, lateral electrode portions and a bottom electrode portion in a space in the gas sensor element, and
wherein an alkali metal oxide is contained in the electrically insulating layer in a total content of 2.5-5 wt %.

2. The gas sensor element according to claim 1, wherein a total content of the at least one metal oxide in the electrically insulating layer is in a range of 2.5-10 wt %.

3. The gas sensor element according to claim 1, wherein the electrically insulating layer further comprises alumina.

4. The gas sensor element according to claim 1, wherein the electrically insulating layer further comprises alumina and silica.

5. The gas sensor element according to claim 1, wherein the alkali metal oxide includes an oxide of Li, Na, or K.

6. The gas sensor element according to claim 1, wherein the alkaline earth metal oxide includes an oxide of Mg, Ca, Sr, or Ba.

7. The gas sensor element according to claim 1, wherein the electrically insulating layer of the heater layer is enclosed by the solid electrolyte.

8. The gas sensor element according to claim 1, wherein the at least one pair of electrodes include a first measuring electrode exposed to an external measurement gas and a reference electrode exposed to a reference gas having a reference oxygen concentration.

9. A nitrogen oxide sensor including a gas sensor element defined in claim 1, for measuring an amount of a nitrogen oxide component contained in an external measurement gas.

10. The nitrogen oxide sensor according to claim 9, comprising, in the sensor layer, a first space into which the external measurement gas is introduced from a gas inlet through a first diffusion controlling passage, a second space into which an atmosphere in the first space is introduced through a second diffusion controlling passage, and a reference-gas space in which a reference gas having a reference oxygen concentration is present.

11. The nitrogen oxide sensor according to claim 10, wherein the at least one pair of electrodes comprises a first measuring electrode disposed so as to be in contact with the external measurement gas and a reference electrode disposed so as to be in contact with the reference gas in the reference-gas space, wherein the first measuring electrode, reference electrode and at least one solid electrolyte layer form a first oxygen-partial-pressure detecting means for detecting an electromotive force corresponding to a difference in an oxygen concentration between the measurement gas and the reference gas.

12. The nitrogen oxide sensor according to claim 11, further comprising a second oxygen-partial-pressure detecting means which includes: a second measuring electrode disposed so as to be in contact with the atmosphere in the first space; and a reference electrode disposed so as to be in contact with the reference gas in the reference-gas space, wherein the second measuring electrode, the reference electrode and at least one solid electrolyte layer form the second oxygen-partial-pressure detecting means for detecting an electromotive force corresponding to a difference in an oxygen concentration between the atmosphere in the first space and the reference gas.

13. The nitrogen oxide sensor according to claim 12, further comprising third oxygen-partial-pressure detecting means which includes: a third measuring electrode disposed so as to be in contact with an atmosphere in the second space and a reference electrode disposed so as to be in contact with the reference gas in the reference-gas space, wherein the third measuring electrode, the reference electrode and at least one solid electrolyte layer form the third oxygen-partial-pressure detecting means for detecting an electromotive force corresponding to a difference in an oxygen concentration between the atmosphere in the second space and the reference gas.

14. The nitrogen oxide sensor according to claim 13, further comprising fourth oxygen-partial-pressure detecting means which includes: a fourth measuring electrode which is disposed in the second space and which reduces or decomposes the nitrogen oxide component contained in the atmosphere which has been introduced from the first space; and a reference electrode which is disposed so as to be in contact with the reference gas in the reference-gas space, wherein the fourth measuring electrode, the reference electrode and at least one electrolyte layer form the fourth oxygen-partial-pressure detecting means for detecting an electromotive force corresponding to a difference between an amount of oxygen generated by reduction or decomposition of the nitrogen oxide component contained in the atmosphere which has been introduced from the first space and an amount of oxygen contained in the reference gas.

15. The nitrogen oxide sensor according to claim 10, further comprising main pumping means which includes a first inner pumping electrode and a first outer pumping electrode respectively formed inside and outside of the first space, the main pumping means performing a pumping action with respect to oxygen contained in the measurement gas which has been introduced into the first space from the gas inlet, based on a control voltage applied between the first inner and outer pumping electrodes.

16. The nitrogen oxide sensor according to claim 15, further comprising measuring pumping means which includes: a second inner pumping electrode which is formed inside of the second space and which reduces or decomposes the nitrogen oxide component contained in the atmosphere that has been introduced from the first space, as a result of contact with the atmosphere; and the first outer pumping electrode, the measuring pumping means performing a pumping action with respect to oxygen generated by reduction or decomposition of the nitrogen oxide component contained in the atmosphere which has been introduced from the first space, based on a voltage applied between the second inner pumping electrode and first outer pumping electrode.

17. The nitrogen oxide sensor according to claim 10, further comprising auxiliary pumping means which includes a pair of auxiliary pumping electrodes respectively formed inside and outside of the second space, the auxiliary pumping means performing a pumping action with respect to oxygen contained in the atmosphere which has been introduced from the first space, based on an auxiliary pumping voltage applied between the pair of auxiliary pumping electrodes.

* * * * *